(12) United States Patent
Overheul et al.

(10) Patent No.: US 10,221,387 B2
(45) Date of Patent: *Mar. 5, 2019

(54) INTEGRATED ETHANOL AND BIODIESEL FACILITY

(71) Applicant: Rayeman Elements, Inc., Berthoud, CO (US)

(72) Inventors: Rachel Overheul, Sedgwick, KS (US); Brandon Awtrey, Sedgwick, KS (US); Daniel Johnson, Sedgwick, KS (US)

(73) Assignee: Rayeman Elements, Inc., Berthoud, CO (US)

( * ) Notice: Subject to any disclaimer, the term of this patent is extended or adjusted under 35 U.S.C. 154(b) by 1077 days.

This patent is subject to a terminal disclaimer.

(21) Appl. No.: 14/468,956

(22) Filed: Aug. 26, 2014

(65) Prior Publication Data

US 2015/0125913 A1   May 7, 2015

Related U.S. Application Data

(60) Continuation-in-part of application No. 14/243,352, filed on Apr. 2, 2014, now Pat. No. 8,840,853, which (Continued)

(51) Int. Cl.
*C10L 1/00* (2006.01)
*C12M 1/00* (2006.01)
(Continued)

(52) U.S. Cl.
CPC ............ *C12M 43/02* (2013.01); *C07C 29/80* (2013.01); *C07C 67/03* (2013.01); *C10L 1/02* (2013.01);
(Continued)

(58) Field of Classification Search
CPC ............ C10L 1/026; C10L 2200/0476; C10L 2200/0469; C10L 1/02; C10L 1/023;
(Continued)

(56) References Cited

U.S. PATENT DOCUMENTS 5,710,030 A    1/1998   Anderson
6,355,456 B1   3/2002   Hallberg et al.
(Continued)

FOREIGN PATENT DOCUMENTS

WO    2007/146971    12/2007
WO    2010/088748    8/2010
(Continued)

OTHER PUBLICATIONS https://www.citylab.com/life/2015/07/power-your-car-with-a-biofuel-made-from-beer/397946/ John Metcalfe Jul. 8, 2015 Power your Car with a biofuel made from Beer.*

(Continued)

*Primary Examiner* — Cephia D Toomer
(74) *Attorney, Agent, or Firm* — Doster Greene, LLC

(57) ABSTRACT

An integrated facility for the co-production of ethanol and biodiesel fuel is provided. Ethanol and corn oil, the primary product and a by-product from the ethanol plant, are utilized as feedstocks for a biodiesel plant operating within the same general facility as the corn ethanol plant. By-products of the biodiesel plant, principally crude liquid glycerol and gaseous ethanol or methanol, are recycled to various parts of the ethanol plant.

19 Claims, 2 Drawing Sheets

Related U.S. Application Data is a division of application No. 14/168,174, filed on Jan. 30, 2014, now Pat. No. 8,722,924.

(60) Provisional application No. 61/898,828, filed on Nov. 1, 2013.

(51) Int. Cl.

| | |
|---|---|
| *C12P 7/10* | (2006.01) |
| *C10L 1/02* | (2006.01) |
| *C07C 67/03* | (2006.01) |
| *C07C 29/80* | (2006.01) |
| *C11C 3/00* | (2006.01) |
| *C12P 7/06* | (2006.01) |

(52) U.S. Cl.
CPC .............. *C10L 1/023* (2013.01); *C10L 1/026* (2013.01); *C11C 3/003* (2013.01); *C12M 21/12* (2013.01); *C12P 7/06* (2013.01); *C12P 7/10* (2013.01); *C10L 2200/0469* (2013.01); *C10L 2200/0476* (2013.01); *C10L 2270/023* (2013.01); *C10L 2270/026* (2013.01); *Y02E 50/13* (2013.01); *Y02E 50/16* (2013.01); *Y02E 50/17* (2013.01)

(58) Field of Classification Search
CPC ........ C10L 2270/023; C10L 2270/026; C12M 43/02; C12M 21/12; C12P 7/10; C12P 7/06; Y02E 50/16; Y02E 50/13; Y02E 50/17; C07C 67/03; C07C 29/80; C11C 3/003
See application file for complete search history.

(56) References Cited

U.S. PATENT DOCUMENTS

| | | | |
|---|---|---|---|
| 6,927,048 B2 | 8/2005 | Verser et al. | |
| 7,263,934 B2 | 9/2007 | Copeland et al. | |
| 7,297,236 B1 | 11/2007 | Vander Griend | |
| 7,321,052 B2 | 1/2008 | Miller et al. | |
| 7,524,418 B2 | 4/2009 | Hirl | |
| 7,544,495 B2 | 6/2009 | Wilkening et al. | |
| 7,572,353 B1 | 8/2009 | Vander Griend | |
| 7,604,743 B2 | 10/2009 | Hirl | |
| 7,608,729 B2 | 10/2009 | Winsness et al. | |
| 7,649,086 B2 | 1/2010 | Belanger et al. | |
| 7,857,872 B2 | 12/2010 | Krasutsky et al. | |
| 7,867,365 B2 | 1/2011 | Brown | |
| 7,927,491 B2 | 4/2011 | Kotelko et al. | |
| 7,943,791 B2 | 5/2011 | McNeff | |
| 7,989,646 B2 | 8/2011 | Bakshi | |
| 8,123,822 B2 | 2/2012 | Morgan | |
| 8,152,867 B2 | 4/2012 | Dumenil | |
| 8,153,850 B2 | 4/2012 | Hall et al. | |
| 8,168,037 B2 | 5/2012 | Winsness | |
| 8,207,362 B2 | 6/2012 | Morris | |
| 8,227,015 B2 | 7/2012 | Bruinsma et al. | |
| 8,288,138 B2 | 10/2012 | Birkmire et al. | |
| 8,354,564 B2 | 1/2013 | Brown et al. | |
| 8,454,802 B2 | 6/2013 | Redford | |
| 8,540,880 B1 | 9/2013 | Shah et al. | |
| 8,540,881 B1 | 9/2013 | Shah et al. | |
| 8,546,627 B2 | 10/2013 | Gruber et al. | |
| 8,722,924 B1* | 5/2014 | Overheul | C07C 67/03 44/308 |
| 8,840,853 B1* | 9/2014 | Overheul | C07C 67/03 422/600 |
| 2003/0019736 A1 | 1/2003 | Garman | |
| 2007/0099278 A1 | 5/2007 | Aare | |
| 2007/0117195 A1 | 5/2007 | Warner et al. | |
| 2007/0260078 A1 | 11/2007 | Bhat et al. | |
| 2008/0176298 A1 | 7/2008 | Randhava et al. | |
| 2008/0229653 A1 | 9/2008 | Iversen et al. | |
| 2008/0282606 A1 | 11/2008 | Plaza et al. | |
| 2009/0017164 A1 | 1/2009 | Shisler et al. | |
| 2009/0031615 A1 | 2/2009 | Joshi et al. | |
| 2009/0126262 A1 | 5/2009 | Asthana et al. | |
| 2009/0148920 A1 | 6/2009 | Schreck | |
| 2009/0239185 A1 | 9/2009 | Deline et al. | |
| 2009/0288988 A1 | 11/2009 | Mayeur et al. | |
| 2009/0311374 A1 | 12/2009 | Beaver et al. | |
| 2010/0021980 A1 | 1/2010 | McDonald et al. | |
| 2010/0028484 A1 | 2/2010 | Kriesler et al. | |
| 2010/0155296 A1 | 6/2010 | Aves et al. | |
| 2010/0178675 A1 | 7/2010 | Lawton, Jr. et al. | |
| 2010/0187818 A1* | 7/2010 | Bivins | F01K 17/04 290/2 |
| 2010/0221804 A1 | 9/2010 | Veit et al. | |
| 2010/0252346 A1 | 10/2010 | Khouw et al. | |
| 2010/0260918 A1 | 10/2010 | Wang et al. | |
| 2010/0317091 A1 | 12/2010 | Veit et al. | |
| 2011/0035393 A1 | 2/2011 | Loescher | |
| 2011/0062054 A1 | 3/2011 | Gao et al. | |
| 2011/0126448 A1 | 6/2011 | Dumenil | |
| 2011/0315541 A1 | 12/2011 | Xu | |
| 2012/0048716 A1 | 3/2012 | Sonnek et al. | |
| 2012/0051980 A1 | 3/2012 | Gallop et al. | |
| 2012/0064213 A1 | 3/2012 | Lee | |
| 2012/0142983 A1 | 6/2012 | Vermeiren et al. | |
| 2012/0181161 A1 | 7/2012 | Mahler | |
| 2012/0205324 A1 | 8/2012 | Cantrell et al. | |
| 2012/0240452 A1 | 9/2012 | Erdoes, Jr. et al. | |
| 2012/0279118 A1 | 11/2012 | Blasco Garcia | |
| 2012/0294977 A1 | 11/2012 | Bruinsma et al. | |
| 2012/0301598 A1 | 11/2012 | Karges et al. | |
| 2013/0010987 A1 | 1/2013 | Abolfathi et al. | |
| 2013/0032175 A1 | 2/2013 | Redford | |
| 2013/0131343 A1 | 5/2013 | Purtle et al. | |
| 2013/0164795 A1 | 6/2013 | Lowe et al. | |
| 2013/0216688 A1 | 8/2013 | Bruinsma et al. | |
| 2013/0309738 A1 | 11/2013 | Barr et al. | |

FOREIGN PATENT DOCUMENTS

| | | |
|---|---|---|
| WO | 2011/075671 | 6/2011 |
| WO | 2012/036857 | 3/2012 |
| WO | 2012/125739 | 9/2012 |
| WO | 2012/145230 | 10/2012 |
| WO | 2013/033369 | 3/2013 |

OTHER PUBLICATIONS http://www.triplepundit.com/2009/02/make-biofuel-from-your-home-using-leftover-beer/ Ashwin Seshagiri Feb. 6, 2009 Make Biofuel from your home using leftover Beer.*
http://news.cornell.edu/print/734 Anne Ju Jun. 20, 2012 Researchers convert beer into a better-than-ethanol biofuel.*
Alles, et al. "Integrated Corn-Based Biorefinery: A Study in Sustainable Process Development" Sustainable Development in the Process Industries: Cases and Impact, Edited by Jan Harmsen and Joseph B. Powell; John Wiley & Sons, Inc.; 2010.
Cardona et al. "Fuel ethanol production: Process design trends and integration opportunities" Bioresource Technology 98 (2007) 2415-2457.
Dien et al. "Fermentation of 'Quick Fiber' Produced from a Modified Corn-Milling Process into Ethanol and Recovery of Corn Fiber Oil" Applied Biochemistry and Biotechnology (2004) vol. 113-116.
Leoneta, et al. "Glycerol as a by-product of biodiesel production in Brazil: Alternatives for the use of unrefined glycerol" Renewable Energy 45 (2012) 138-145.
Moser et al. "Biodiesel from Corn Distillers Dried Grains with Solubles: Preparation, Evaluation, and Properties" Bioenergy Research (Jun. 2012), vol. 5, No. 2, pp. 439-449.
Nigam et al. "Production of liquid biofuels from renewable resources" Progress in Energy and Combustion Science 37 (2011) 52-68.
Shi et al. "Bioresource Technology" Bioresource Technology 128 (2013) 100-106.
Biomass Program: Integrated Corn-Based Bio-Refinery; U.S. Dept of Energy Brochure 2006.

(56) References Cited

OTHER PUBLICATIONS

Wang et al. "Effect of the Corn Breaking Method on Oil Distribution between Stillage Phases of Dry-Grind Corn Ethanol Production" J. Agric. Food Chem. 2008, 56, 9975-9980.

Wukovits et al. "Energy self supply of a bio-ethanol production plant by utilisation of renewable energy from residues from feedstock and ethanol production" CHISA 2006—17th International Congress of Chemical and Process Engineering (2006). (Abstract only).

\* cited by examiner

INTEGRATED ETHANOL AND BIODIESEL FACILITY

CROSS-REFERENCE TO RELATED APPLICATION

This application is a continuation in part of application Ser. No. 14/243,352, filed Apr. 2, 2014, which is a division of application Ser. No. 14/168,174, filed Jan. 30, 2014, now U.S. Pat. No. 8,722,924, and claims the benefit of provisional application Ser. No. 61/898,828, filed Nov. 1, 2013, and all of these applications are incorporated by reference herein in their entirety.

BACKGROUND OF THE INVENTION

Field of the Invention

The present invention generally pertains to an integrated facility for the co-production of ethanol and biodiesel fuel. In particular, corn oil isolated from the whole stillage of a corn ethanol distillation process is utilized as a feedstock for a biodiesel plant, along with alcohol (e.g., methyl alcohol, ethyl alcohol, and mixtures thereof), operating within the same general facility as the corn ethanol plant. By-products of the biodiesel plant, such as liquid crude glycerol and gaseous or liquid alcohols, can be utilized in various parts of the ethanol plant thereby increasing the operating efficiency thereof.

Description of the Prior Art

Corn oil is a by-product of a corn ethanol production. The corn oil is generally carried through the fermentation and distillation portions of a corn ethanol plant into the whole stillage that is removed from the distillation system. The whole stillage is commonly separated into a thin stillage, which includes the corn oil, and a cake that can be dried to produce dried distillers grains with solubles (DDGS), which can be used as an animal feed. The thin stillage can be processed to remove moisture therefrom and form nutritive syrup that can also be used as an animal feed material. Alternatively, the corn oil may be extracted from the thin stillage and be made a saleable product.

The corn oil extracted from the thin stillage has many industrial uses, such as in soaps, paints, rustproofing materials, inks, textiles, and insecticides. Corn oil can also be used as a feedstock in the production of alternative fuels such as biodiesel and renewable diesel. Biodiesel refers to a vegetable oil- or animal fat-based diesel fuel comprising long-chain alkyl (methyl, ethyl, or propyl) esters. Biodiesel is generally not considered to be a full replacement of conventional petrodiesel for use in most diesel engines. Rather, it is generally blended with petrodiesel for use in the retail diesel fuel marketplace. Renewable diesel, on the other hand, is produced by hydrotreatment of corn oil, for example, resulting in a hydrocarbon fuel that is very similar to petroleum diesel in its chemical composition.

A number of reaction schemes exist for conversion of corn oil into renewable diesel. Hydrotreating is one such process in which the corn oil feedstock is reacted with hydrogen under elevated temperature and pressure to change the chemical composition of the feed-stock. In the case of renewable diesel, hydrogen is introduced to the feedstock in the presence of a catalyst convert the triglyceride molecules into paraffinic hydrocarbons. In addition to creating a fuel that is very similar to petrodiesel, this process creates other hydrocarbon by-products including lower hydrocarbon fuel gas compounds (e.g., methane, ethane, propane, and butane) and higher hydrocarbon naphtha.

Production of biodiesel usually involves using corn oil and alcohol as feedstocks to a biodiesel reactor where the corn oil first undergoes an acid esterification reaction whereby the free fatty acids are converted to an alkyl ester through the introduction of a strong acid (e.g., sulfuric acid). The triglycerides are then subjected to a base-catalyzed reaction in the presence of strong base (e.g., KOH) and the alcohol feedstock, in order to form alkyl esters. The ester reaction product is then separated from the glycerol fraction which also contained excess alcohol used in the transesterification reaction.

Generally, the corn oil and/or alcohol feedstocks are produced at a plant location remote from the biodiesel facility, thus requiring transport of these feedstocks via pipeline, railway tankers, or tanker trucks. This added transportation cost increases the overall expense in the manufacture of biodiesel and decreases its competitiveness with petrodiesel as an alternative fuel source.

The following references describe various types of ethanol and biodiesel production methods: U.S. Pat. Nos. 6,927,048, 7,608,729, 7,649,086, 8,152,867, 8,227,015, 8,454,802, US 2008/0176298, US2009/0017164, US2009/0311374, US2010/0021980, US2010/0028484, US2010/0178675, US2010/0260918, US2011/0126448, US2012/0051980, US2012/0064213, US2012/0301598, US2013/0032175, US2013/0102045, US2013/0130343, US2013/0164795, WO2007/146971, WO2012036857, WO2012/125739, WO2012/145230, and WO2013033369.

SUMMARY OF THE INVENTION

The present invention overcomes many of the problems outlined above and provides improved processes and plant systems for the co-production of ethanol and biodiesel fuel in combined facilities having both an ethanol plant and a biodiesel plant, wherein the plants are located in close proximity allowing various products and by-products from each plant to be easily transferred to the other plant as desired to increase the efficiency of the overall, dual-plant facility.

In one aspect of the invention, an integrated process for the co-production of ethanol and biodiesel fuel comprises the steps of fermenting a corn feedstock to produce an ethanol-containing beer and distilling the ethanol-containing beer within distillation apparatus of an ethanol plant, thereby producing ethanol and a corn oil product. Thereafter, the corn oil product is directed from the ethanol plant to a proximal biodiesel fuel plant; the corn oil product and an alcohol are used as joint feedstocks in the diesel plant, where the corn oil product and alcohol are reacted to produce a biodiesel fuel and by-products comprising an alcohol, e.g., ethanol and/or methanol, and glycerol. These by-products, which generally is low in ester compound concentration, are then transferred back to the ethanol plant for use therein.

In one embodiment, the transferring step comprises the steps of initially condensing the gaseous alcohol by-product to generate a condensed liquid by-product. This liquid by-product is directed back to the ethanol plant for mixing with the ethanol-containing beer. Alternately, the gaseous alcohol by-product may be combined with the $CO_2$-containing overhead from the beer prior to stripping of the $CO_2$. Still further, this gaseous by-product may 92 be combined with a process steam overhead generated by an evaporation system used to recover the corn oil by-product.

In another aspect of the invention, the liquid crude glycerol generated as a by-product in the diesel fuel plant is directed back to the ethanol plant for post-fermentation mixing with the beer, and/or may be added to a concentrated thin stillage product, which is further processed to generate a syrup.

A still further aspect of the invention involves use of the bottoms of the biodiesel distillation apparatus of the diesel fuel plant. These bottoms, principally comprising high boiling components and unreacted mono-, di-, and triglycerides, can be added to the solids output from the ethanol plant (e.g., a cake), which are normally used to produce animal feeds.

The invention also provides integrated plants for the co-production of ethanol and biodiesel fuel corresponding to the foregoing method aspects of the invention. Thus, such a facility may include an ethanol plant comprising fermentation apparatus operable to produce an ethanol-containing beer from a corn feedstock and distillation apparatus operable to produce ethanol and a corn oil product from the ethanol-containing beer; and a biodiesel plant comprising a reactor assembly operably coupled with the ethanol plant apparatus to receive at least some of the corn oil product from the ethanol plant, and to react the corn oil product with alcohol to produce biodiesel fuel and outputs such as the gaseous and/or liquid by-product containing alcohol; the liquid crude glycerol; and/or the bottoms from a biodiesel distillation device. Transfer structure(s), typically standard interconnecting transfer pipes or lines, are provided to direct one or more of the biodiesel outputs from the biodiesel plant as desired to the ethanol plant for use therein, in some or all of the ethanol plant locations described previously.

It will be appreciated that the present invention maximizes the efficiencies of both the ethanol and diesel fuel plants forming a part of the overall production facilities contemplated by the invention. Thus, the principal products of the ethanol plant, namely ethanol and corn oil, need not be transported great distances thereby giving significant savings. Nor is there a need for commercial sourcing of the alcohol or corn oil needed for the biodiesel fuel plant.

DETAILED DESCRIPTION OF THE PREFERRED EMBODIMENT

Figure 1:
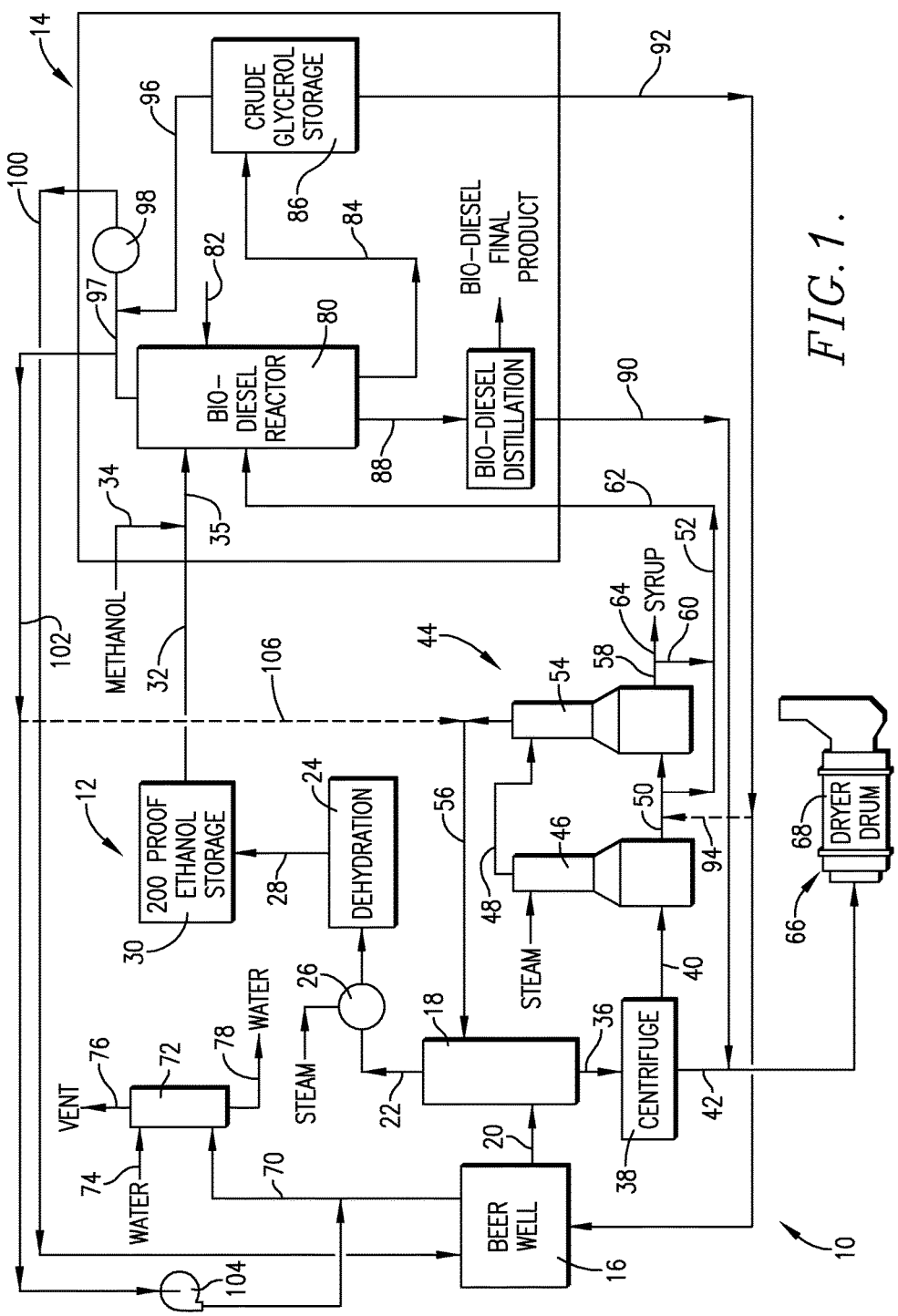
FIG. 1 is a schematic diagram of an integrated ethanol and biodiesel production facility in accordance with the invention, and illustrating several optional features.

Turning now to FIG. 1, an integrated ethanol and biodiesel production facility 10 is illustrated. The facility 10 broadly comprises an ethanol plant 12 and a biodiesel plant 14. As illustrated, the ethanol plant 12 and biodiesel plant 14 are co-located so that products and by-products of each facility can be readily shared, thereby reducing equipment and operating costs for the overall facility 10. As used herein, the term "by-product" refers not only to reaction products, but materials fed to a reaction vessel in excess that are later recovered from the reaction vessel and separated from the reaction products.

Ethanol plant 12 may be configured in a conventional manner, with the starting bio-mass material undergoing initial processing and fermentation to produce an ethanol-containing "beer." In the particular embodiment illustrated, the ethanol plant 12 utilizes a biomass material as the source of carbohydrates and sugars for the fermentation process. A plant or vegetable oil is an important by-product of the ethanol plant 12, inasmuch as this by-product forms the feedstock to the biodiesel plant 14, so that the biomass material should contain suitable amounts of plant oils. Exemplary biomass feed materials include corn, sorghum, and pearl millet. In the U.S., corn is the predominant feedstock for fuel ethanol production. Accordingly, the description set forth below is made with respect to corn and corn by-products. However, it should be understood that this description is exemplary only, and should not be taken as a limitation on the scope of the present invention.

The preparation and fermentation of corn feedstock within ethanol plant 12 may be carried out in any number of apparatus and according to any number of methods known to those skilled in the art, and thus need not be fully described herein. In any case, following fermentation, the resultant ethanol-containing beer may be stored within a beer well 16 while it awaits further processing. Typically, the beer comprises from about 10-20% by volume ethanol, more preferably about 15% by volume ethanol. The beer also contains from about 5-20% by weight solids, more preferably about 10% by weight solids.

The beer is fed to distillation apparatus 18 via stream 20 for separation and recovery of the ethanol contained therein. Distillation apparatus 18, which may comprise one or more distillation columns, produces an overhead stream 22 primarily comprising ethanol and some water (e.g., from about 80-99% by volume ethanol, preferably from about 90-98% by volume ethanol, and most preferably about 95% by volume ethanol), with the balance of the stream primarily including water. In order to be suitable for use as fuel-grade ethanol, the remaining water needs to be removed from overhead stream 22. This water separation may be accomplished by means of a dehydration unit 24, which can be equipped with molecular sieve technology to achieve this separation. In certain embodiments, the molecular sieve comprises an alumino silicate material. In certain embodiments, stream 22 is condensed so that a portion can be refluxed back to apparatus 18, however, this need not always be the case. In those embodiments in which stream 22 was previously condensed, the stream should be vaporized before it is passed to dehydration unit 24. This vaporization can be accomplished by one or more heat exchangers 26 feed with steam supplied via a plant distribution header. A substantially pure ethanol stream 28 (i.e., greater than 99% by volume ethanol, or approximately 200 proof) exits dehydration unit 24 and is stored in a storage vessel 30 to await further processing.

As illustrated in FIG. 1, one of the feedstock inputs to the biodiesel plant 14 contains alcohol. This typically is the ethanol from line 32. However, if desired, methanol from line 34 may be used as the alcohol feedstock, either alone or mixed with the ethanol in line 32. Thus, the alcohol-containing feedstock 35 to plant 14 is either ethanol, methanol, or a mixture of methanol and ethanol.

The bottoms from distillation apparatus 18 comprise a whole stillage stream 36. Several products can be produced from whole stillage stream 36 including corn oil, a nutritive corn syrup, and dried distillers grains with solubles (DDGS). The whole stillage stream 36 may be separated by a centrifuge 38 into a thin stillage stream 40 and a cake stream 42. The thin stillage stream 40 generally comprises between about 5% to about 10% by weight solids, and more preferably about 7% by weight solids. The balance of the thin stillage comprises mainly water and corn oil. The thin stillage is concentrated within a multiple-effect evaporator 44. Steam from the steam distribution header is introduced into a first effect 46 in indirect heat exchange relationship with the thin stillage stream 40. Moisture is evaporated from the thin stillage and removed from first effect 46 as process steam stream 48. The concentrated stillage product is removed from first effect 46 via line 50 and a portion of the corn oil contained therein is separated as stream 52. The separation of the corn oil may be achieved through the use of a mechanical separation device (not shown), such as a decanter system (e.g., the TRICANTER from Flottweg Separation Technology, Germany), or a disc stack unit. The concentrated stillage product (minus the corn oil that was removed) is passed through a second effect 54 wherein steam from stream 48, through indirect heat exchange, causes a portion of the moisture contained within the concentrated stillage product to evaporate. This vapor is returned to distillation apparatus 18 via stream 56.

The stillage product now comprises a viscous syrup and is withdrawn from the second effect 54 via stream 58. Additional corn oil is removed from the viscous syrup in stream 58 by means of a secondary separation device (not shown), and this additional corn oil is directed via line 60 to stream 52. This forms a combined stream 62 which is directed to biodiesel plant 14 as a feedstock input thereto. The syrup having the oil removed therefrom is recovered as a product stream 64.

In an alternate embodiment of the present invention, the corn oil may be extracted prior to fermentation. For example, the corn oil may be extracted via pressing or solvent extraction prior to fermentation. In such case, the processing of the thin stillage occurs as mentioned above, with the exception of corn oil recovery.

The cake stream 42 from centrifuge 38 is conveyed toward drying apparatus 66 in which moisture is removed and DDGS produced. Drying apparatus 66 comprises one or more dryer drums 68 that are supplied by a hot air stream from a conventional fuel-fired heater (not shown).

The gaseous overhead from beer well 16 comprises carbon dioxide. This overhead is directed via line 70 to a $CO_2$ scrubber 72 having a water inlet line 74. In scrubber 72, the $CO_2$ is stripped and vented through vent line 76, and an underflow line 78 principally containing water, along with some alcohol (in certain embodiments, approximately 3% ethanol), is generated.

As previously described, there are two feedstock inputs to plant 14, namely alcohol feedstock 35 and corn oil stream 62. These feedstocks are directed to biodiesel reactor system 80 where the corn oil first undergoes an acid esterification reaction whereby the free fatty acids are converted to alkyl esters through the introduction of a strong acid (e.g., sulfuric acid) via line 82. The triglycerides are then subjected to base-catalyzed reaction in the presence of a strong base (e.g., KOH) and the alcohol feedstock 35, in order to form alkyl (methyl, ethyl and/or propyl) esters and glycerol. The ester reaction product is then directed to a wash/dry tank (not shown) forming a part of system 80, in which the esters are separated from the glycerol. In alternate embodiments, the washing and drying of the ester reaction product may be conducted within the same vessel where the transesterification reaction is conducted thereby reducing the capital costs associated with a separate wash/dry tank. The latter fraction, also containing excess alcohol used in the transesterification reactions, is directed via line 84 to a storage tank 86. In certain embodiments, the composition of the stream in line 84 comprises less than 10% esters by weight, preferably less than 7.5% esters by weight, more preferably less than 5% esters by weight, even more preferably less than 1% esters by weight, and most preferably the composition is substantially free of esters. The ester fraction is sent via line 88 to a biodiesel distillation column where the biodiesel final product is separated for use, and the distillation bottoms (principally comprising high boiling components and unreacted mono- and polyglycerides, e.g., di- and triglycerides) are sent via line 90 and are combined with the cake stream 42 prior to drying thereof In certain embodiments, the composition of the distillation bottoms in line 90 comprises less than 10% biodiesel product by weight, preferably less than 7.5% biodiesel product by weight, more preferably less than 5% biodiesel product by weight, even more preferably less than 1% biodiesel product by weight, and most preferably is substantially free of biodiesel product. In certain preferred embodiments, the biodiesel final product is a fuel comprised of mono-alkyl esters of long chain fatty acids, commonly designated B100, and meeting the requirements of ASTM D 6751, incorporated by reference herein.

A liquid fraction of the alcohol/glycerol mixture within storage tank 86 is directed via line 92 to beer well 16, as shown, where it is mixed, post-fermentation, with the ethanol-containing beer. The ethanol-containing beer within beer well 16 is sent subsequently to distillation apparatus 18. In certain embodiments, the composition of the stream in line 92 comprises less than 10% esters by weight, preferably less than 7.5% esters by weight, more preferably less than 5% esters by weight, even more preferably less than 1% esters by weight, and most preferably is substantially free of esters. In certain embodiments, the composition of the stream in line 92 is comprises glycerol as the predominant component. In other embodiments, the stream in line 92 comprises greater than 50% glycerol by weight, greater than 75% glycerol by weight, greater than 90% glycerol by weight, or greater than 95% glycerol by weight. In alternate embodiments, some or all of the contents of line 92 may be directed through line 94 to the concentrated stillage line 50 for mixing therein, prior to entering the second effect 54. In the effect 54, the alcohol is vaporized along with water, and this water/alcohol mixture is returned via stream 56 to distillation apparatus 18. The gaseous alcohol-containing overheads from reactor system 80 and tank 86 are directed through lines 96 and 97 to vent condenser 98. These alcohol-containing overheads may also comprise water vapor that is carried along with the alcohol. The resultant condensed alcohol liquid fraction from condenser 98 is then sent through line 100, and ultimately to beer well 16 for further processing in plant 12. In an alternative embodiment, some or all of the gaseous overheads in lines 96 and 97 are directed through a line 102 equipped with a blower 104 for mixing with the beer well overhead 70 prior to entrance into scrubber 72. In a still further alternate embodiment, some of all of the contents of line 102 may be directed via line 106 for mixture with the contents of stream 56 directed from evaporator 54 to distillation apparatus 18. In certain embodiments, the composition of the condensed liquid fraction in line 100 or the vapor stream carried in line 102 comprises less than 10% esters by weight, preferably less than 8% esters by weight, more preferably less than 5% esters by weight, even more preferably less than 1% esters by weight, and most preferably is substantially free of esters. In certain embodiments, the composition of the condensed liquid fraction in line 100 or the vapor stream carried in line 102 comprises one or more alcohol compounds (e.g., ethanol, methanol, or a combination thereof) as the predominant component(s). In other embodiments, the stream in line 100 or the vapor stream carried in line 102 comprises greater than 50% alcohol compounds by weight, greater than 75% alcohol compounds by weight, or greater than 90% alcohol compounds by weight.

In conventional biodiesel plants, the crude glycerol directed to tank 86 contains methanol produced in the biodiesel reaction, and this methanol must be separated before the glycerol is disposed of or used as a commercial product. This requires additional separation equipment, which represents a significant capital expense, and moreover the glycerol/methanol separation requires an energy input. In the present invention, however, use is made of the existing separation equipment present in the ethanol plant to further process the glycerol/methanol mixture, namely distillation apparatus 18, second effect 54, associated recovery lines 58, 60, and 62, overhead vent line 96, condenser 98, and recovery line 100. As such, capital equipment costs are reduced and very little additional energy is required.

Figure 2:
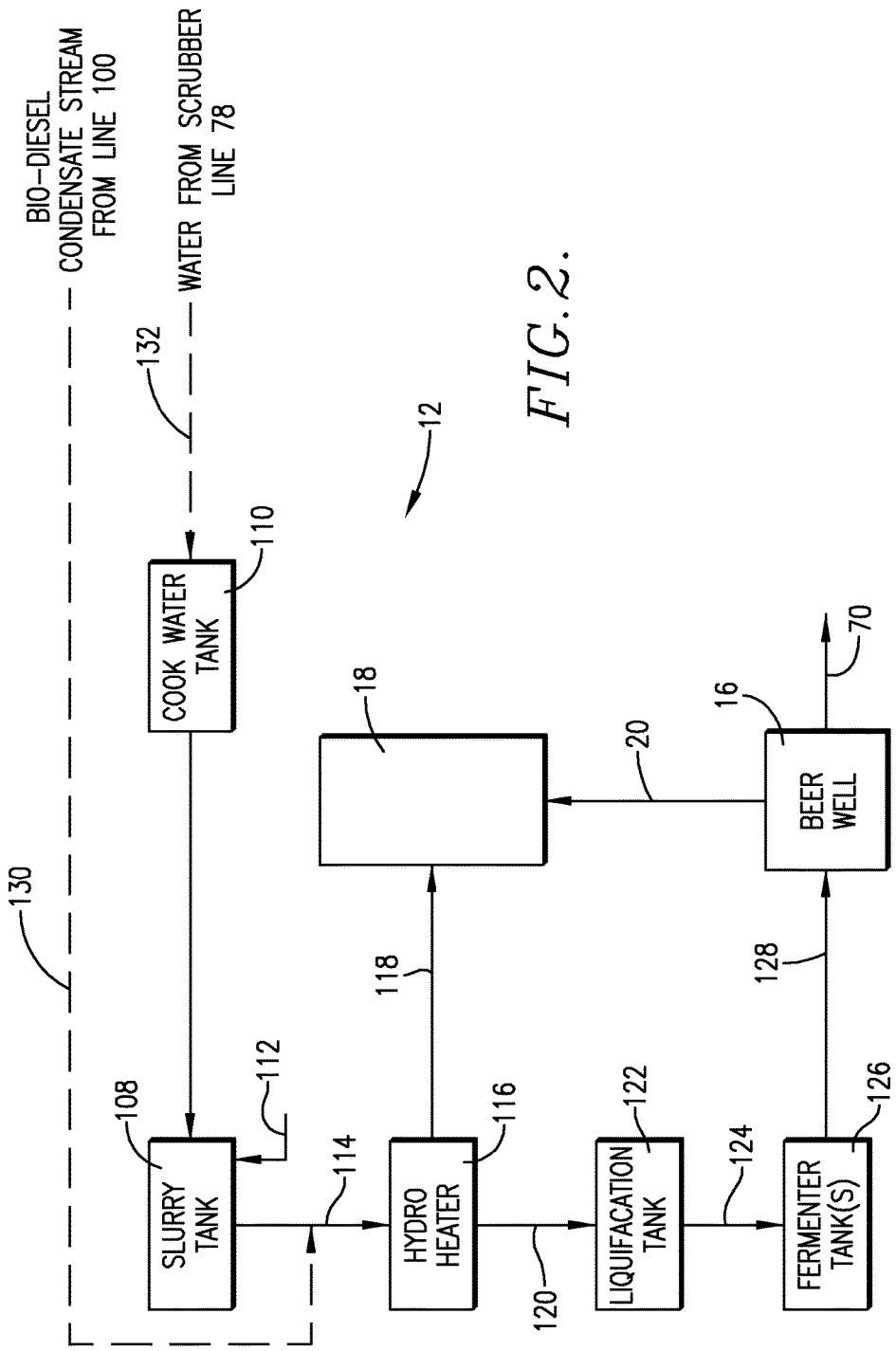
FIG. 2 is a schematic diagram of another embodiment of the invention, illustrating a further optional feature for the combined production facility.

FIG. 2 illustrates a still further embodiment of the invention, wherein the condensate stream from line 100 and the water from scrubber line 78 are integrated into the plant 12 in a different manner. Although not shown in FIG. 1, the plant 12 additionally includes a number of conventional components upstream of beer well 16 and distillation apparatus 18. Specifically, a slurry tank 108 is provided, which is used to create the initial corn/water slurry, using water from a cook water tank 110. The slurry within tank 108 is also steam-heated via line 112. The heated slurry is then passed through line 114 to a hydroheater 116, wherein the slurry is further steam-heated. A fraction of the heated slurry is then fed to apparatus 18 via line 118, with the remainder being directed through line 120 to liquefaction tank 122. The output from tank 122 is directed through line 124 to fermenter tank(s) 126 to yield the ethanol-containing beer sent via line 128 to beer well 16. In certain embodiments, the glycerol by-product from line 92 may be mixed with the ethanol-containing beer within beer well 16. Thus, the glycerol is mixed with the beer post-fermentation and the glycerol is not utilized as a fermentation feedstock or added to fermenter tank(s) 126. In further embodiments, fermentation of the corn feedstock is substantially complete at the time the glycerol by-product in line 92 is mixed with the ethanol-containing beer.

In the FIG. 2 embodiment, the condensate stream from line 100 is directed through line 130 for mixture with the output from slurry tank 108 in line 114. Furthermore, the water from scrubber line 78 is fed through line 132 to cook water tank 110.

It is understood that the various integrations between biodiesel plant 14 and ethanol plant 12 described above may be carried out jointly, individually, or in any combination thereof, as the requirements of any given facility 10 dictate. However, use of the alcohol and corn oil outputs from the ethanol plant 12, coupled with the use of the biodiesel fuel plant by-products, is preferred and is believed to the give maximum efficiency advantages.

We claim:

1. An integrated facility for the co-production of ethanol and biodiesel fuel using corn as a feedstock, comprising:
    an ethanol plant comprising fermentation apparatus operable to produce an ethanol-containing beer from said feedstock and a distillation apparatus operable to produce ethanol and a corn oil product from said ethanol-containing beer;
    a biodiesel plant comprising a reactor assembly operably coupled with said ethanol plant to receive at least some corn oil product from the ethanol plant, and to react said corn oil with alcohol to produce biodiesel fuel and one or more by-products selected from the group consisting of methanol, ethanol, glycerol, and combinations thereof;
    structure for transferring at least one stream of said by-products comprising less than 10% esters by weight to said ethanol plant downstream of said fermentation apparatus for mixing with said ethanol-containing beer prior to distillation within said distillation apparatus or mixing with a stillage stream of said distillation apparatus undergoing concentration within said ethanol plant;
    a centrifuge provided within the ethanol plant and coupled with the distillation apparatus for receiving biodiesel distillation bottoms comprising a whole stillage stream and separating the whole stillage stream into a thin stillage stream, which includes an insoluble solids portion in a range of about 5% to 10% by weight, and a cake stream to produce whole stillage byproducts including at least dried distiller grains;
    a biodiesel distillation apparatus provided within the biodiesel plant and coupled with the reactor assembly for receiving the at least one stream of said by-product comprising less than 10% esters by weight for combining the at least one stream of said by-product comprising less than 10% esters with the cake stream after exiting the centrifuge and prior to entering a drying process; and
    a drying apparatus coupled with and downstream of the centrifuge to receive the combination of the cake stream and the at least one stream of said by-product comprising less than 10% esters to produce a substantially dry final product comprising the dried distiller grains.

2. The facility of claim 1, said ethanol-containing beer contained within a beer well, said beer well generating a gaseous overhead comprising $CO_2$, at least one of said by-products being directed in gaseous form from said biodiesel plant to said ethanol plant for combination with said beer well overhead.

3. The facility of claim 1, said ethanol plant comprising the distillation apparatus operable to create the whole stillage stream and ethanol, a separation assembly operable to generate the thin stillage stream, and an evaporator operable to separate said corn oil product from said thin stillage, and to generate a steam overhead, at least one of said by-product from said biodiesel plant being mixed in gaseous form with said steam overhead.

4. The facility of claim 1, said distillation apparatus operable to create a whole stillage product, a separation assembly comprising a multiple-effect evaporator including first and second effects, operable to produce said corn oil product from said whole stillage product, said glycerol supply being sent from said biodiesel plant to said ethanol plant for mixture with a concentrated thin stillage product from said first effect.

5. The facility of claim 1, said reactor assembly operable to generate a supply of liquid crude glycerol, at least some of said glycerol supply being sent from said biodiesel plant to said ethanol plant for mixture with said ethanol-containing beer.

6. The facility of claim 1, said ethanol plant including an apparatus for creating a heated corn/water slurry, the apparatus being operable to condense at least one of said by-products to generate a condensed by-product containing ethanol or methanol, said condensed by-product being sent from said biodiesel plant to said ethanol plant for mixture with said heated corn/water slurry.

7. The facility of claim 1, said ethanol plant including a slurry tank for creating a heated corn/water slurry, said ethanol-containing beer generating a gaseous overhead comprising $CO_2$, the ethanol plant including a $CO_2$ scrubber operable to receive said ethanol-containing beer overhead and to create a water stream, at least part of said water stream from the $CO_2$ scrubber used as a part of said corn/water slurry.

8. An integrated process for the co-production of ethanol and biodiesel fuel, comprising the steps of:
   fermenting a corn feedstock to produce an ethanol-containing beer;
   distilling said ethanol-containing beer within a distillation apparatus of an ethanol plant, and producing ethanol and a corn oil product;
   directing the corn oil product from said ethanol plant to a biodiesel fuel plant, and reacting said corn oil product with alcohol to produce a biodiesel fuel and one or more by-products selected from the group consisting of glycerol, ethanol, methanol, and combinations thereof;
   transferring at least one stream of said by-products comprising less than 10% esters by weight to said ethanol plant for post-fermentation mixing with said ethanol-containing beer prior to distillation within said distillation apparatus or mixing with a stillage stream of said distillation apparatus undergoing concentration within said ethanol plant;
   transferring biodiesel distillation bottoms comprising a whole stillage stream to a centrifuge provided within the ethanol plant and coupled with the distillation apparatus for separation of the whole stillage stream into a thin stillage stream, which includes an insoluble solids portion in a range of about 5% to 10% by weight, and a cake stream to produce whole stillage byproducts including at least dried distiller grains;
   transferring the at least one stream of said by-product comprising less than 10% esters by weight to a biodiesel distillation apparatus provided within the biodiesel plant and coupled with the reactor assembly for combining the at least one stream of said by-product comprising less than 10% esters with the cake stream after exiting the centrifuge and prior to entering a drying process; and
   transferring the combination of the cake stream and the at least one stream of said by-product comprising less than 10% esters to a drying apparatus coupled with and downstream of the centrifuge to produce a substantially dry final product comprising the dried distiller grains.

9. The process of claim 8, said distilling step creating a whole stillage product, and said process comprising the step of recovering said corn oil product from said whole stillage product.

10. The process of claim 8, said ethanol-containing beer contained within a beer well, said beer well generating a gaseous overhead comprising $CO_2$, said transferring step to said ethanol plant for post-fermentation comprising the step of directing at least one of said by-products in gaseous form for combination with said beer well overhead.

11. The process of claim 10, said combined beer well overhead being passed through a $CO_2$ scrubber to separate said $CO_2$ and create a water stream comprising said at least one of said by-products, said water stream being employed to supply at least part of the water for the
   generation of a heated corn/water slurry within said ethanol plant.

12. The process of claim 8, said transferring step to said ethanol plant for post-fermentation comprising the step of condensing one or more of said by-products to generate a condensed by-product comprising ethanol or methanol or a combination thereof, and thereafter directing said condensed by-product for mixture with said ethanol-containing beer.

13. The process of claim 8, said distilling step creating a whole stillage product, said whole stillage product being treated to generate a thin stillage product, said corn oil product being separated from said thin stillage product by evaporation of the thin stillage product to generate said corn oil product and an evaporator steam overhead, said transferring step to said ethanol plant for post-fermentation comprising the step of transferring at least one of said by-products in gaseous form for mixture with said evaporator steam overhead.

14. The process of claim 8, wherein said reaction step generates a supply of liquid crude glycerol, and including the step of transferring at least some of said liquid crude glycerol to said ethanol plant for use therein.

15. The process of claim 14, said transferring step comprising the step of transferring at least some of said liquid crude glycerol for mixture with said ethanol-containing beer.

16. The process of claim 14, said distilling step creating a whole stillage product, said whole stillage product being treated to generate a thin stillage product, said corn oil product being separated from said thin stillage product in a multiple-effect evaporator comprising first and second effects, said step of transferring said liquid crude glycerol comprising the step of mixing the crude glycerol with a concentrated thin stillage product from said first effect.

17. The process of claim 8, said ethanol plant operation including the step of generating a heated corn/water slurry, said transferring step comprising the step of condensing at least one of said by-products to generate a condensed by-product containing ethanol or methanol or combinations thereof, and transferring said condensed by-product for mixture with said heated corn/water slurry.

18. The process of claim 17, said alcohol comprising ethanol, methanol, or a mixture thereof.

19. The process of claim 8, said biodiesel fuel plant producing the biodiesel distillation bottoms stream comprising one or more members selected from the group consisting of mono-, di-, and triglycerides, said distillation bottoms stream being transferred to said ethanol plant for use therein.

* * * * *